(12) United States Patent
Moon et al.

(10) Patent No.: US 11,051,980 B2
(45) Date of Patent: Jul. 6, 2021

(54) CAPSULORHEXIS APPARATUS

(71) Applicant: TI INC., Goyang-si (KR)

(72) Inventors: Sung Hyuk Moon, Daegu (KR); Jae Wook Yang, Busan (KR)

(73) Assignee: TI INC., Goyang-si (KR)

( * ) Notice: Subject to any disclaimer, the term of this patent is extended or adjusted under 35 U.S.C. 154(b) by 93 days.

(21) Appl. No.: 15/104,974

(22) PCT Filed: Jan. 14, 2014

(86) PCT No.: PCT/KR2014/000396
§ 371 (c)(1),
(2) Date: Jun. 16, 2016

(87) PCT Pub. No.: WO2015/093678
PCT Pub. Date: Jun. 25, 2015

(65) Prior Publication Data
US 2017/0000646 A1    Jan. 5, 2017

(30) Foreign Application Priority Data

Dec. 16, 2013  (KR) .................. 10-2013-0156651

(51) Int. Cl.
*A61F 9/007*    (2006.01)
(52) U.S. Cl.
CPC ...... *A61F 9/00754* (2013.01); *A61F 9/00745* (2013.01)
(58) Field of Classification Search
CPC .............. A61F 9/00754; A61F 9/00745; A61B 17/32056; A61B 2018/141; A61B 17/221; A61B 2017/2212; A61B 1/320567
(Continued)

(56) References Cited

U.S. PATENT DOCUMENTS

| 5,269,787 A | 12/1993 | Cozean, Jr. |
| 5,336,227 A * | 8/1994 | Nakao .............. A61B 17/32056 |
| | | 600/106 |

(Continued)

FOREIGN PATENT DOCUMENTS

| CN | 102026600 | 4/2011 |
| CN | 102458320 | 5/2012 |

(Continued)

OTHER PUBLICATIONS

International Search Report for PCT/KR2014/000396 dated Sep. 16, 2014 from Korean Intellectual Property Office.

(Continued)

*Primary Examiner* — Majid Jamialahmadi
(74) *Attorney, Agent, or Firm* — Ladas & Parry, LLP

(57) ABSTRACT

Provided is a capsulorhexis apparatus for incising an anterior capsule covering a crystalline lens by being inserted into an incision site of a cornea, the capsulorhexis apparatus including: an anterior capsule incision portion which has a closed curve shape, is inserted into the incision site of the cornea to incise the anterior capsule located below the cornea to a circle, and generates heat by using high frequency vibration to incise the anterior capsule; a body portion which is externally exposed when the anterior capsule incision portion incises the anterior capsule while slidingly moving in the body portion, and is internally inserted when the anterior capsule incision portion does not incise the anterior capsule; and a button portion which is formed on one side of the body portion and slidingly moves the anterior capsule incision portion inside the body portion.

6 Claims, 3 Drawing Sheets

(58) Field of Classification Search
USPC .................................................. 606/107, 113
See application file for complete search history.

(56) References Cited

U.S. PATENT DOCUMENTS

| | | | | |
|---|---|---|---|---|
| 5,947,979 | A * | 9/1999 | Ouchi | A61B 17/32056 |
| | | | | 606/113 |
| 6,231,578 | B1 * | 5/2001 | Rajhansa | A61B 17/22012 |
| | | | | 606/113 |
| 6,264,663 | B1 * | 7/2001 | Cano | A01N 59/00 |
| | | | | 606/110 |
| 6,383,194 | B1 | 5/2002 | Pothula | |
| 2001/0027312 | A1 * | 10/2001 | Bacher | A61B 17/2909 |
| | | | | 606/1 |
| 2005/0228403 | A1 * | 10/2005 | Ho | A61B 10/0266 |
| | | | | 606/113 |
| 2006/0129166 | A1 * | 6/2006 | Lavelle | A61B 17/221 |
| | | | | 606/113 |
| 2010/0094278 | A1 | 4/2010 | Jia et al. | |
| 2010/0241130 | A1 | 9/2010 | Deli et al. | |
| 2010/0312232 | A1 | 12/2010 | Jia et al. | |
| 2011/0213359 | A1 | 9/2011 | Ben-Nun et al. | |
| 2013/0158573 | A1 | 6/2013 | Zaidman et al. | |
| 2013/0197548 | A1 * | 8/2013 | Keller | A61B 18/08 |
| | | | | 606/166 |
| 2013/0296876 | A1 * | 11/2013 | Jordan | A61F 9/00745 |
| | | | | 606/107 |

FOREIGN PATENT DOCUMENTS

| | | |
|---|---|---|
| CN | 103347469 | 10/2013 |
| JP | 1-232946 | 9/1989 |
| JP | 2008-538306 | 10/2008 |
| JP | 2009-504313 | 2/2009 |
| JP | 2012-505067 | 3/2012 |
| JP | 2012-511407 | 5/2012 |
| JP | 2012-515017 | 7/2012 |
| JP | 2012-528675 A | 11/2012 |
| JP | 2013-528447 A | 7/2013 |
| KR | 10-2010-0016724 A | 2/2010 |
| KR | 10-2010-0121583 A | 11/2010 |
| KR | 10-2011-0084887 A | 7/2011 |
| KR | 10-1649105 | 8/2016 |
| WO | 2012-127465 A2 | 9/2012 |

OTHER PUBLICATIONS

International Preliminary Report on Patentability (Chapter I) for PCT/KR2014/000396 dated Jun. 21, 2016 and its English translation from WIPO.
Written Opinion of the International Searching Authority for PCT/KR2014/000396 dated Sep. 16, 2014 and its English translation from Google Translate.
Decision to Grant dated Nov. 24, 2017 for Japanese Patent Application No. 2016-540982 and its English translation from Global Dossier.
Office Action dated Aug. 25, 2017 for Japanese Patent Application No. 2016-540982 and its English translation from Global Dossier.
Office Action dated Apr. 25, 2017 for Japanese Patent Application No. 2016-540982 and its English translation from Global Dossier.
Office Action dated Apr. 18, 2017 for Chinese Patent Application No. 201480075567.3 and its English translation by Google Translate.
Office Action dated Jan. 22, 2020 for Indian Patent Application No. 201647023635.
Office Action dated Jun. 30, 2020 for Vietnamese Patent Application No. 1-2016-02644 and its English translation by Google Translate.

* cited by examiner

[FIG. 1]
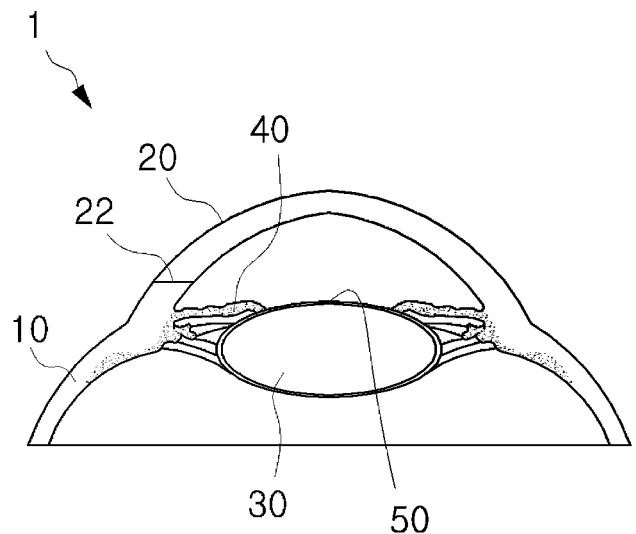
[FIG. 2]
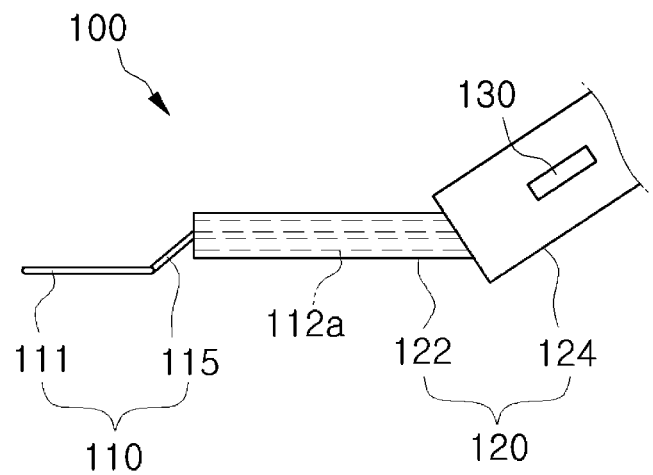

[FIG. 3]
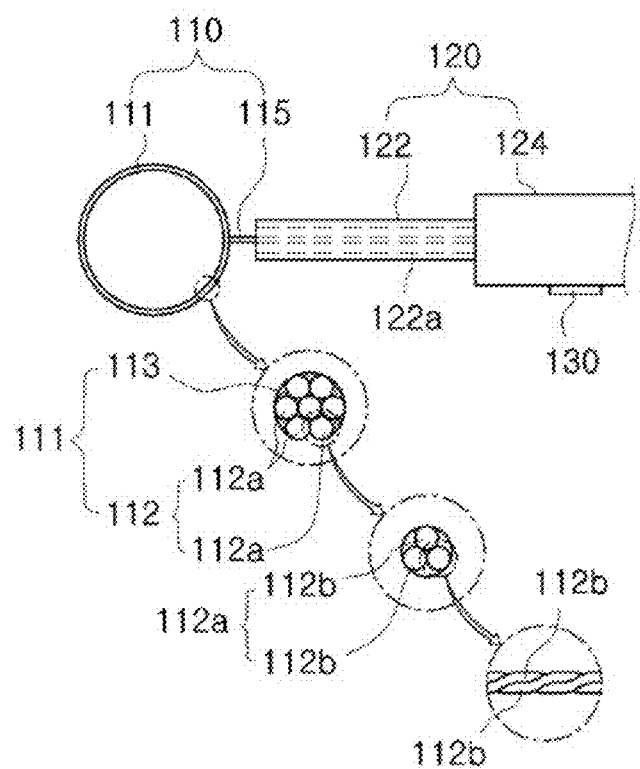
[FIG. 4]
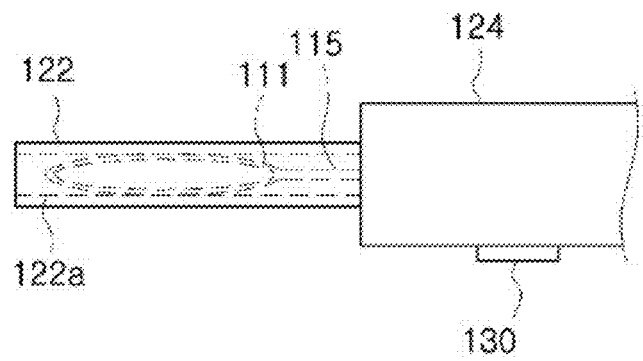

[FIG. 5]
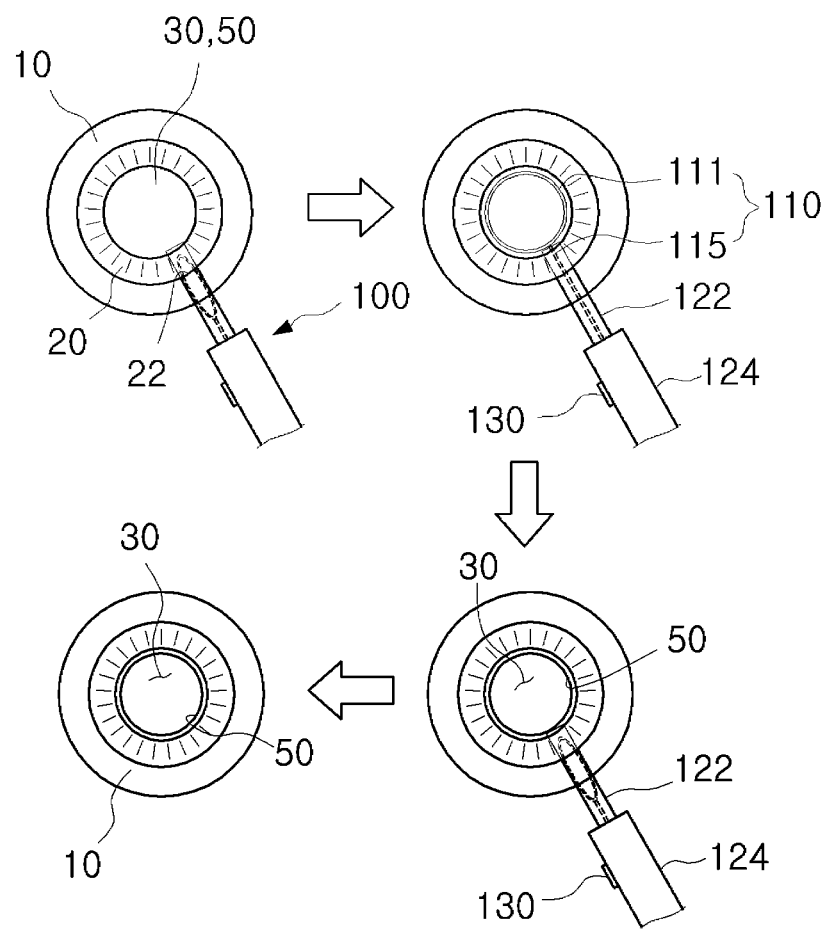

CAPSULORHEXIS APPARATUS

CROSS REFERENCE TO PRIOR APPLICATIONS

This application is a National Stage Application of PCT International Patent Application No. PCT/KR2014/000396 filed on Jan. 14, 2014, under 35 U.S.C. § 371, which claims priority to Korean Patent Application No. 10-2013-0156651 filed on Dec. 16, 2013, which are all hereby incorporated by reference in their entirety.

TECHNICAL FIELD

The present invention relates to a capsulorhexis apparatus, and more particularly, to a capsulorhexis apparatus for neatly and precisely incising, into a circle, a front surface of an anterior capsule covering a crystalline lens of an eyeball.

BACKGROUND ART

Referring to the Background Art of KR 2010-0016724, an eye (or an eyeball 1) forming a body is an organ securing a clear view by detecting intensity and a wavelength of light, and includes, as shown in FIG. 1, a cornea 20 formed to cover the outside of a sclera 10 and formed of transparent avascular tissues to refract light, a colorless and transparent crystalline lens 30 functioning as a lens of a camera, an iris 40 containing a pigment to determine a color of a pupil and functioning as an aperture to adjust an amount of light entering the eye, and a retina (not shown) formed of transparent nervous tissues and corresponds to a film of a camera.

Meanwhile, the crystalline lens 30 forming the eye as such corresponds to a lens of a camera, and similar to a case in which resolution of a photograph is low when the lens is dirty, when the crystalline lens 30 is cloudy, an object looks blurry since light does not satisfactorily enter the eye. A cataract is developed when the crystalline lens 30 is cloudy due to several reasons as such.

When a cataract is developed, eyesight is prevented from being decreased or lost through immediate treatment, and the cataract is treated mostly by incising a lens capsule 50 covering the crystalline lens 30 to pulverize the crystalline lens 30 located therein by using ultrasonic waves, removing the pulverized crystalline lens 30 by using ultrasonic waves or the like, and then inserting an artificial crystalline lens (not shown) to replace the removed crystalline lens 30.

In other words, the sclera 10 or the cornea 20 is incised at a width of about 2 to 3 mm by using a diamond knife or the like, an incision tool (not shown) obtained by bending an end of a needle is inserted through the incision window W to scrape a front surface of the lens capsule 50 to a certain shape L, the crystalline lens 30 exposed accordingly is pulverized by using ultrasonic waves, the pulverized crystalline lens 30 is sucked and externally discharged, and then the artificial crystalline lens is inserted and fixed instead of the discharged crystalline lens 30.

However, when a general incision tool is used, an operator inserts a needle into the incision window W and scrapes the lens capsule 50 a plurality of times so as to incise the front surface of the lens capsule 50.

Accordingly, by using such a general incision tool, it is difficult to neatly and precisely incise the lens capsule 50 to a suitable size and shape (in particular, a circle), and in server cases, an anterior capsule may rupture radially and the artificial crystalline lens (not shown) may not be inserted properly, thereby generating endophthalmitis or requiring a reporperation to replace the artificial crystalline lens.

Also, since the incision tool needs to be moved a plurality of times very carefully to incise the front surface of the lens capsule 50, the surgery is very difficult and time consuming.

DETAILED DESCRIPTION OF THE INVENTION

Technical Problem

The present invention provides a capsulorhexis apparatus for neatly and precisely incising, into a circle, a front surface of an anterior capsule while incising the anterior capsule covering a crystalline lens of an eyeball into a circle, and in addition, enabling the surgery to be safely and conveniently performed.

Technical Solution

According to an aspect of the present invention, there is provided a capsulorhexis apparatus for incising an anterior capsule covering a crystalline lens by being inserted into an incision site of a cornea, the capsulorhexis apparatus including: an anterior capsule incision portion which has a closed curve shape, is inserted into the incision site of the cornea to incise the anterior capsule located below the cornea to a circle, and generates heat by using high frequency vibration to incise the anterior capsule; a body portion which is externally exposed when the anterior capsule incision portion incises the anterior capsule while slidingly moving in the body portion, and is internally inserted when the anterior capsule incision portion does not incise the anterior capsule; and a button portion which is formed on one side of the body portion and slidingly moves the anterior capsule incision portion inside the body portion.

The anterior capsule incision portion may include: a circular incision tool which incises the anterior capsule to a circle; and a moving member which has one end connected to the circular incision tool to slidingly move the circular incision tool. The circular incision tool may include: a wire portion in which a plurality of wire members are twisted in a straw rope shape to have elasticity; and a coating portion which is coated outside the wire portion.

The wire member may be obtained by twisting a plurality of minute wires in a straw rope shape. The plurality of minute wires may include a metallic material to generate heat while having elasticity.

The body portion may include: a guide portion in which the anterior capsule incision portion slidingly moves and which has one end inserted into the incision site of the cornea to guide the anterior capsule incision portion to pass the incision site of the cornea; and a body which has one end connected to the guide portion and in which the moving member slidingly moves, wherein the button portion is provided on one surface of the body.

The guide portion may include a silicon material, and a moving hole through which the anterior capsule incision portion slidingly moves may be formed at a center portion of the guide portion. The one end of the guide portion, which is connected to the body, may be slantly connected to the body.

Advantageous Effects

A capsulorhexis apparatus according to the present invention has following effects.

First, since a front surface of an anterior capsule covering a crystalline lens is precisely incised into a circle, a revision surgery caused by an operation failure is prevented and in addition, the surgery is safely and easily performed.

Second, a circular incision tool of an anterior capsule incision portion, which incises an anterior capsule, is formed by twisting a plurality of minute wires and wire members, thereby not only preventing the circular incision tool from being deformed by heat, but also improving elasticity of the circular incision tool, such that the circular incision tool is not discarded after one surgery but used several times, thereby reducing expenses.

Third, by incising an anterior capsule as a circular incision tool of an anterior capsule incision portion generates heat by using a high frequency instead of a current, deformation of the circular incision tool caused by self-heating is prevented and a time taken by the circular incision tool to be heated is reduced, and thus a surgery time may be reduced.

DESCRIPTION OF THE DRAWINGS

FIG. 1 is a view schematically illustrating an eyeball of a body.

FIG. 2 is a front view schematically illustrating a capsulorhexis apparatus according to the present invention.

FIG. 3 is a plan view of the capsulorhexis apparatus of FIG. 2.

FIG. 4 is a view of an interior capsule incision portion of FIG. 2 being inserted into a guide portion of a body portion.

FIG. 5 is a view illustrating processes of a capsulorhexis apparatus according to the present invention incising an anterior capsule.

BEST MODE

Hereinafter, the present invention will be described more fully with reference to the accompanying drawings, in which exemplary embodiments of the invention are shown. The terms or words used herein must not be interpreted in their common or dictionary definitions, but must be interpreted in the meanings and concept corresponding to the aspect of the present invention, based on the principle that the inventor(s) can suitably define the concept of terms in order to describe the invention in the best manner.

FIG. 1 is a view schematically illustrating an eyeball of a body, FIG. 2 is a front view schematically illustrating a capsulorhexis apparatus according to the present invention, FIG. 3 is a plan view of the capsulorhexis apparatus of FIG. 2, FIG. 4 is a view of an interior capsule incision portion of FIG. 2 being inserted into a guide portion of a body portion, and FIG. 5 is a view illustrating processes of a capsulorhexis apparatus according to the present invention incising an anterior capsule.

Referring to FIGS. 1 through 5, a capsulorhexis apparatus 100 according to the current embodiment is for incising the anterior capsule 50 covering the crystalline lens 30 by being inserted into an incision site (not shown) of the cornea 20 or the sclera 10, and includes an anterior capsule incision portion 110, a body portion 120, and a button portion 130.

The anterior capsule incision portion 110 has a closed curve shape, incises the anterior capsule 50 to a circle by being inserted into an incision site 22 of the cornea 20 or an incision site (not shown) of the sclera 10, and incises the anterior capsule 50 by heating moisture of the anterior capsule 50 contacting the anterior capsule incision portion 110 in a short period of time (within 1 second) by using heat generated via high frequency vibration.

The anterior capsule incision portion 110 includes a circular incision tool 111 and a moving member 115. The circular incision tool 111 incises the anterior capsule 50 to a circle, and the moving member 115 slidingly moves the circular incision tool 111 as one end of the moving member 115 is connected to the circular incision tool 111.

The circular incision tool 111 includes a wire portion 112 and a coating portion 113. The wire portion 112 may be formed by twisting a plurality of wire members 112a in a straw rope shape to have elasticity. When the wire portion 112 includes one wire member 112a instead of the plurality of wire members 112a, it is difficult for the circular incision tool 111 to sufficiently maintain an original shape after passing through a guide portion 122 of the body portion 120, and the wire member 112a deforms due to heat and thus is unable to be reused for precise incision.

The coating portion 113 is coated on an outer top portion of the wire portion 112. The coating portion 113 prevents endothelial cells of the cornea 20 from being damaged by heat of the circular incision tool 111, and may have a color contrasting a color of the eyeball so that an operator easily determines whether the circular incision tool 111 inserted into the incision site 22 of the cornea 20 is precisely located at a front center portion of the anterior capsule 50.

The wire member 112a may be formed by twisting a plurality of minute wires 112b in a straw rope shape. When the minute wires 112b are twisted in a straw rope shape, the elasticity is further increased, and the minute wires 112b may include a metallic material that has elasticity and in which a current easily moves so as to generate heat while having elasticity.

The anterior capsule incision portion 110 may be exposed outside the body portion 120 when incising the anterior capsule 50 while slidingly moving inside the body portion 120, and inserted into the body portion 120 when not incising the anterior capsule 50.

The body portion 120 includes the guide portion 122 and a body 124. The guide portion 122 guides the anterior capsule incision portion 110 to slidingly move in the body portion 120 and to pass the incision site 22 of the cornea 20.

The guide portion 122 includes a silicon material, and a moving hole 122a through which the anterior capsule incision portion 110 slidingly moves is formed at a center portion of the guide portion 122. As the moving hole 122a is formed at the guide portion 122, the anterior capsule incision portion 110 is externally exposed from the inside of the moving hole 122a when incising the anterior capsule 50 while slidingly moving inside the moving hole 122a and maintains a state of being inserted into the moving hole 122a when not incising the anterior capsule 50.

One end of the guide portion 122 is connected to the body 124, the moving member 115 of the anterior capsule incision portion 110 slidingly moves inside the body 124, and a moving hole (not shown) through which the moving member 115 slidingly moves may be formed inside the body 124.

The guide portion 122 connected to the body 124 may be slantly connected to the body 124, and one end of the moving member 115 connected to the circular incision tool 111 may be slantly formed.

Since the body 124 and the guide portion 122 are slantly connected and the moving member 115 is slantly formed, an operator easily performs operations of inserting the guide portion 122 into the incision site 22 of the cornea 20 or the incision site (not shown) of the sclera 10 and then incising the anterior capsule 50 to a circle by using the circular incision tool 111.

The button portion 130 that slidingly moves the anterior capsule incision portion 110 inside the body portion 120 is formed on one surface of the body portion 120. When the operator manipulates the button portion 130, the anterior capsule incision portion 110 that slidingly moves according to manipulation of the button portion 130 is exposed from the inside of the body portion 120 to incise the anterior capsule 50 to a circle or to be inserted into the body portion 120.

Processes of incising the anterior capsule 50 by using the capsulorhexis apparatus 100 according to the present invention will now be briefly described.

First, after the operator forms the incision site 22 in the cornea 20 or the incision site (not shown) in the sclera 10 by using an incision tool, the operator inserts one end of the guide portion 122 to the incision site. When the operator manipulates the button portion 130 after inserting the guide portion 122, the anterior capsule incision portion 110 is exposed outside the body portion 120 and is located at an upper portion of the anterior capsule 50 to be incised.

When the anterior capsule incision portion 110 located at the upper portion of the anterior capsule generates heat by using high frequency, the circular incision tool 111 of the anterior capsule incision portion 110 quickly incises the anterior capsule 50 to a circle, and when the operator manipulates the button portion 130 in a reverse direction after incising the anterior capsule 50 to a circle, the anterior capsule incision portion 110 is inserted into the body portion 120 and thus the anterior capsule 50 the operator desires to incise to a circle is quickly and precisely incised to a circle.

Accordingly, the front surface of the anterior capsule 50 covering the crystalline lens 30 may be precisely incised to a circle, and thus not only a revision surgery caused by a surgery failure may be prevented but also the surgery may be performed safely and easily. Also, since the circular incision tool 111 of the anterior capsule incision portion 110 incising the anterior capsule 50 is formed by twisting the plurality of minute wires 112b and the plurality of wire members 112a, the circular incision tool 111 is not only prevented from being deformed by heat but also has high elasticity, and thus the circular incision tool 111 may not be discarded after one surgery and is used several times to reduce expenses. Also, since the circular incision tool 111 of the anterior capsule incision portion 110 incises the anterior capsule 50 after generating heat by using a high frequency instead of a current, deformation caused by self-heating of the circular incision tool 111 is prevented and a time taken by the circular incision tool 111 to be heated is reduced, and thus a surgery time is reduced.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

The present invention may be used to incise an anterior capsule during a cataract surgery.

The invention claimed is:

1. A capsulorhexis apparatus for incising an anterior capsule covering a crystalline lens by being inserted into an incision site of a cornea, the capsulorhexis apparatus comprising:
an anterior capsule incision portion which has a closed curve shape, and is configured to be inserted into the incision site of the cornea to incise the anterior capsule located below the cornea to a circle;
a body portion into which the anterior capsule incision portion is inserted, the anterior capsule incision portion configured to be externally exposed to incise the anterior capsule; and
a button portion which is formed on one side of the body portion and slidingly moves the anterior capsule incision portion inside the body portion,
wherein the anterior capsule incision portion comprises:
a circular incision tool maintaining a completely closed circle and configured to be in contact with an upper portion of the anterior capsule when exposed outside the body portion, wherein the circular incision tool exposed outside the body portion generates heat by using high frequency vibration and is configured to incise the upper portion of the anterior capsule to the completely closed circle; and
a moving member having one end connected to the circular incision tool,
wherein the circular incision tool comprises:
a wire portion which is formed by a plurality of wire members twisted in a straw rope shape to have elasticity, wherein each of the plurality of wire members is obtained by twisting a plurality of minute wires in a straw rope shape; and
a coating portion coated on an outer top portion of the wire portion, wherein the coating portion has a color configured to contrast with a color of an eyeball to allow an operator to determine whether the circular incision tool is precisely located at a front center portion of the anterior capsule.

2. The capsulorhexis apparatus of claim 1, wherein the plurality of minute wires include a metallic material to generate heat while having elasticity.

3. The capsulorhexis apparatus of claim 1, wherein the body portion comprises:
a guide portion in which the anterior capsule incision portion slidingly moves and which has one end configured to be inserted into the incision site of the cornea to guide the anterior capsule incision portion to pass the incision site of the cornea; and
a body which has one end connected to the guide portion and in which the moving member slidingly moves,
wherein the button portion is provided on one surface of the body.

4. The capsulorhexis apparatus of claim 3, wherein the guide portion includes a silicon material, and
a moving hole through which the anterior capsule incision portion slidingly moves is formed at a center portion of the guide portion.

5. The capsulorhexis of claim 3, wherein a second end of the guide portion, which is connected to the body, is slantly connected to the body.

6. A capsulorhexis apparatus for incising an anterior capsule covering a crystalline lens by being inserted into an incision site of a cornea, the capsulorhexis apparatus comprising:
an anterior capsule incision portion which has a closed curve shape, and is configured to be inserted into the incision site of the cornea to incise the anterior capsule located below the cornea to a circle;
a body portion into which the anterior capsule incision portion is inserted, the anterior capsule incision portion configured to be externally exposed to incise the anterior capsule; and a button portion which is formed on one side of the body portion and slidingly moves the anterior capsule incision portion inside the body portion, wherein the anterior capsule incision portion comprises:

a circular incision tool maintaining a completely closed circle and configured to be in contact with an upper portion of the anterior capsule when exposed outside the body portion in order to incise the upper portion of the anterior capsule to the completely closed circle; and a moving member having one end connected to the circular incision tool, wherein the circular incision tool comprises:

a wire portion which is formed by a plurality of wire members twisted in a straw rope shape to have elasticity, wherein each of the plurality of wire members is obtained by twisting a plurality of minute wires in a straw rope shape; and a coating portion coated on an outer top portion of the wire portion, wherein the coating portion has a color configured to contrast with a color of an eyeball to allow an operator to determine whether the circular incision tool is precisely located at a front center portion of the anterior capsule.

* * * * *